(12) United States Patent
Hsieh

(10) Patent No.: US 6,522,255 B1
(45) Date of Patent: Feb. 18, 2003

(54) HANDLE SENSOR FOR DETECTING SIGNALS FROM HUMAN BODY TO A SIGNAL PROCESSING CIRCUIT

(76) Inventor: Steve Hsieh, 5th Fl., No. 9, Alley 24, Lane 68 Kwany Fu Road, Sec. 1, San Chung City Taipei Hsien (CN)

( * ) Notice: Subject to any disclaimer, the term of this patent is extended or adjusted under 35 U.S.C. 154(b) by 0 days.

(21) Appl. No.: 09/032,846

(22) Filed: Mar. 2, 1998

(51) Int. Cl.$^7$ ............................................... G08B 21/00
(52) U.S. Cl. ..................... 340/657; 340/653; 340/661; 340/432; 482/8; 482/901; 600/587
(58) Field of Search .................. 340/657, 653, 340/660, 661, 432, 573.1; 482/1, 2, 3, 4, 5, 8, 44, 901; 600/587

(56) References Cited

U.S. PATENT DOCUMENTS

| | | | |
|---|---|---|---|
| 3,323,367 A | * 6/1967 | Searle | 600/587 |
| 3,702,113 A | * 11/1972 | Blockley | 600/384 |
| 4,319,581 A | * 3/1982 | Cutter | 600/520 |
| 5,318,487 A | * 6/1994 | Golen et al. | 482/5 |
| 5,365,934 A | * 11/1994 | Leon et al. | 600/517 |
| 5,527,239 A | * 6/1996 | Abbondanza | 482/8 |

* cited by examiner

Primary Examiner—Julie Lieu
(74) Attorney, Agent, or Firm—Pro-Techtor InterNational Services

(57) ABSTRACT

In a signal processing circuit the detector of which is handle sensor, the tubular handle sensor thereof includes an insulating inner layer and a holdable conducting outer layer, the bottom and the right and left sides of the conducting outer layer are enclosed by said insulating inner layer and are connected with a conductor through the insulating inner layer. The conductor is further connected to a rated power source so to form a current stub by which the rated power source may supply power to a working switch. The conductor has another electric loop for being connected to a processing circuit and the working voltage of the processing circuit is supplied by the controlling of the working switch. As the human body holds the handle sensor, the working switch may transfer a voltage required to the processing circuit so that the pulse from the human body by the handle sensor or the differential potential from the hands of the human may be sequentially amplified, filtered, shaping and output in the processing circuit. The output signal may be received and displayed by a receiving processing display device.

5 Claims, 16 Drawing Sheets

HANDLE SENSOR FOR DETECTING SIGNALS FROM HUMAN BODY TO A SIGNAL PROCESSING CIRCUIT

BACKGROUND OF THE INVENTION

1. Field of the Invention

The present invention relates to a handle type sensor, especially to a handle for supplying the signal of the pulse of or the potential difference of the hands, and a signal processing circuit using the handle sensor type detector.

2. Description of the Prior Art

Recently, although some exercising equipment for being operated or held by hand are installed with sensing devices for sensing the pulse signal, the technologies are simple and poor, and in general, the handle of an exercising equipment, for example an exercising bicycle, is firstly tied with a layer of insulating cloth or a insulating tape and then a layer of metal piece is further tied on said layer of insulating cloth or insulating tape for contacting with a human body and sensing the pulse signal of human body, however, it is difficult to fix the cloth and metal piece on the tubular metal handle, and the metal piece is easy to become rusty and feel cool and cloth may absorb water so that it is easy to wear by the friction from the rotation of the metal piece, thus the insulating function is gradually disappeared. Therefore, either the signal reacted by the metal piece is shorted due to contact with a handle, or the signal that the metal sense the pulse signal of the human body becomes weak and is not easy to be taken out since the cloth absorbs water. Apparently, this question will threat the human body during thunder or when the power line supplied to the display device has drained out, while the metal is easy to be interfered by electromagnetic waves from other gymnastic machine.

In order to solve the problem that the metal piece is easy to oxidize, in an improvement, a conducting rub is seemed above the cloth instead of the metal piece for inducing the pulse signal of human body. The problems of poor holding feeling and easy oxidization of metal piece are solved, and there are the advantages of higher friction and tighter engagement than those between the metal piece and the cloth layer, however, the smooth conducting rub could not fast drain sweat and is not easy to be held, and right and left lateral ends of the conducting rub have no design for preventing the sweat flow, thus the sweat may flow to the cloth along the right and left lateral ends of the conducting rub so that the cloth will lose the function of insulation. Although if an insulating rub is used to replace the cloth layer, then a part of the problem may be solved, the sweat still may flow to the insulating inner layer along the right, and left lateral ends of the conducting rub for contacting the metal handle of the gymnastic machine so that the signal of the human body will be probably bypassed, and since the right and left lateral ends of the conducting rub have not been sealed, thus these sections are easy to be interfered by other electromagnetic field.

SUMMARY OF THE INVENTION

Accordingly, the main object of the present invention is to provide a tubular handle sensor in which an insulating inner layer is used to enclose a conducting outer layer except that the upper surface.

Another object of the present invention is to provide a handle sensor in which the surface of a conducting outer layer has a plurality of grooves for draining sweat.

A further object of the present invention is to provide a handle sensor having an insulating plug for sealing the right lateral end of the handle sensor for further decreasing the outside electromagnetic interference.

A further object of the present invention is to provide a signal processing circuit in which the handle sensor thereof is used as a detector.

A further object of the present invention is to a provide a processing circuit of handle sensor having a working switch, said working switch is employed to control the power supply of a rated power source to a processing circuit so that said processing circuit will not operate as the handle sensor is not held by a human body, while as the human body has held the handle sensor, the processing circuit will operate and then the pulse from the human body holding the handle sensor or the differential potential of two hands may be amplified, filtered, shaped and outputted.

In a handle sensor and a signal processing circuit the detector of which is said handle sensor, the tubular handle sensor thereof includes an insulating inner layer and a holdable conducting outer layer, the bottom and the right and left sides of the conducting outer layer are enclosed by an insulating inner layer and are connected with a conductor through the insulating inner layer. The conductor is further connected to a rated power source so to form a current stub by which the rated power source may supply power to a working switch. The conductor has another electric loop for being connected to a processing circuit and the working voltage of the processing circuit is supplied by the controlling of the working switch. As the handle sensor has not been held by a human body, the working switch will not output any voltage, thus the processing circuit will not operate. As the human body holds said handle sensor, the working switch will transfer a voltage required to the processing circuit so that the pulse or the differential potential from the hands of the human body, any one of which, may be sequentially amplified, filtered, shaped and outputted in the processing circuit. The output signal may be received and displayed by a receiving processing display device. The surface of the conducting outer layer has a plurality of grooves.

The present invention will be better understood and its numerous objects and advantages will become apparent to those skilled in the art by referencing to the following drawings in which:

DETAILED DESCRIPTION OF THE PREFERRED EMBODIMENT

Figure 1:
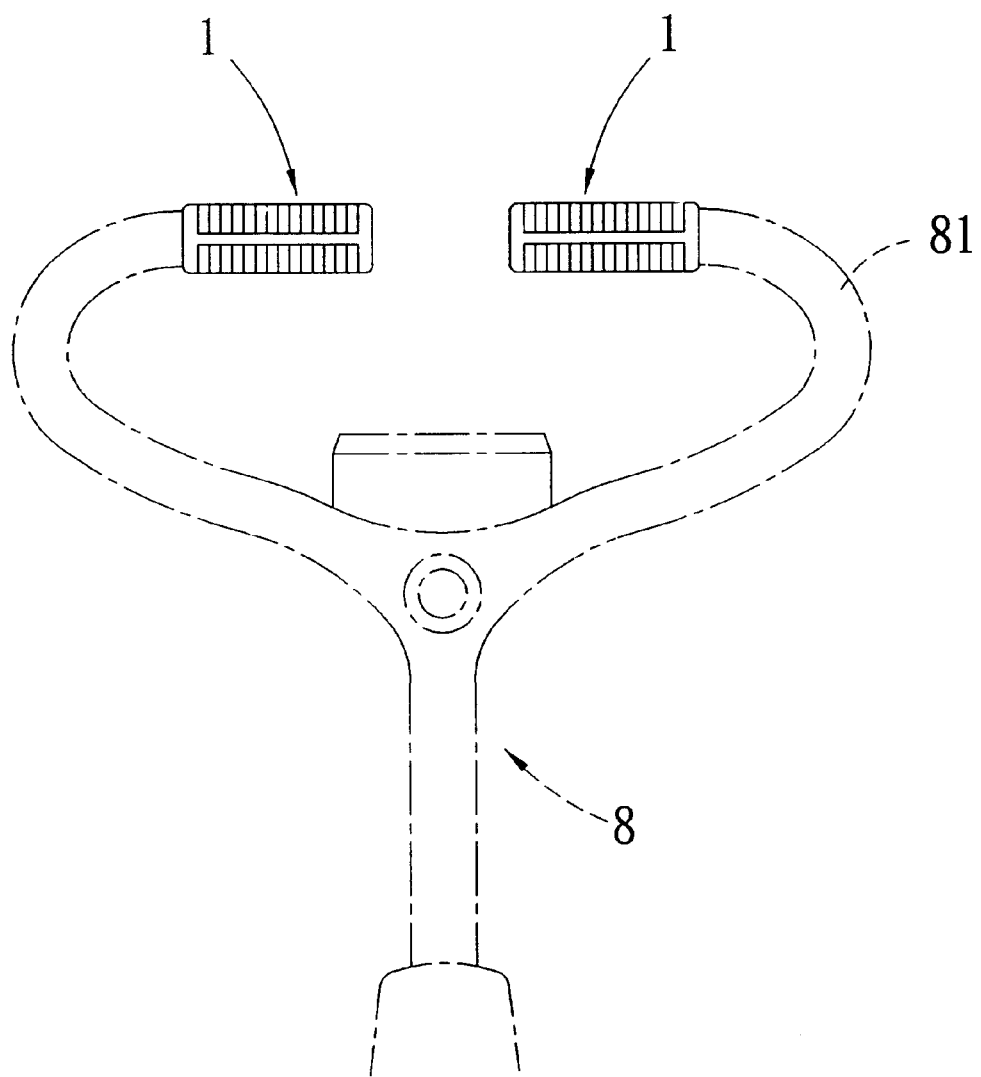
FIG. 1 is a schematic view shown that the handle sensor of the present invention is installed on the handle of a gymnastic machine.
Figure 2:
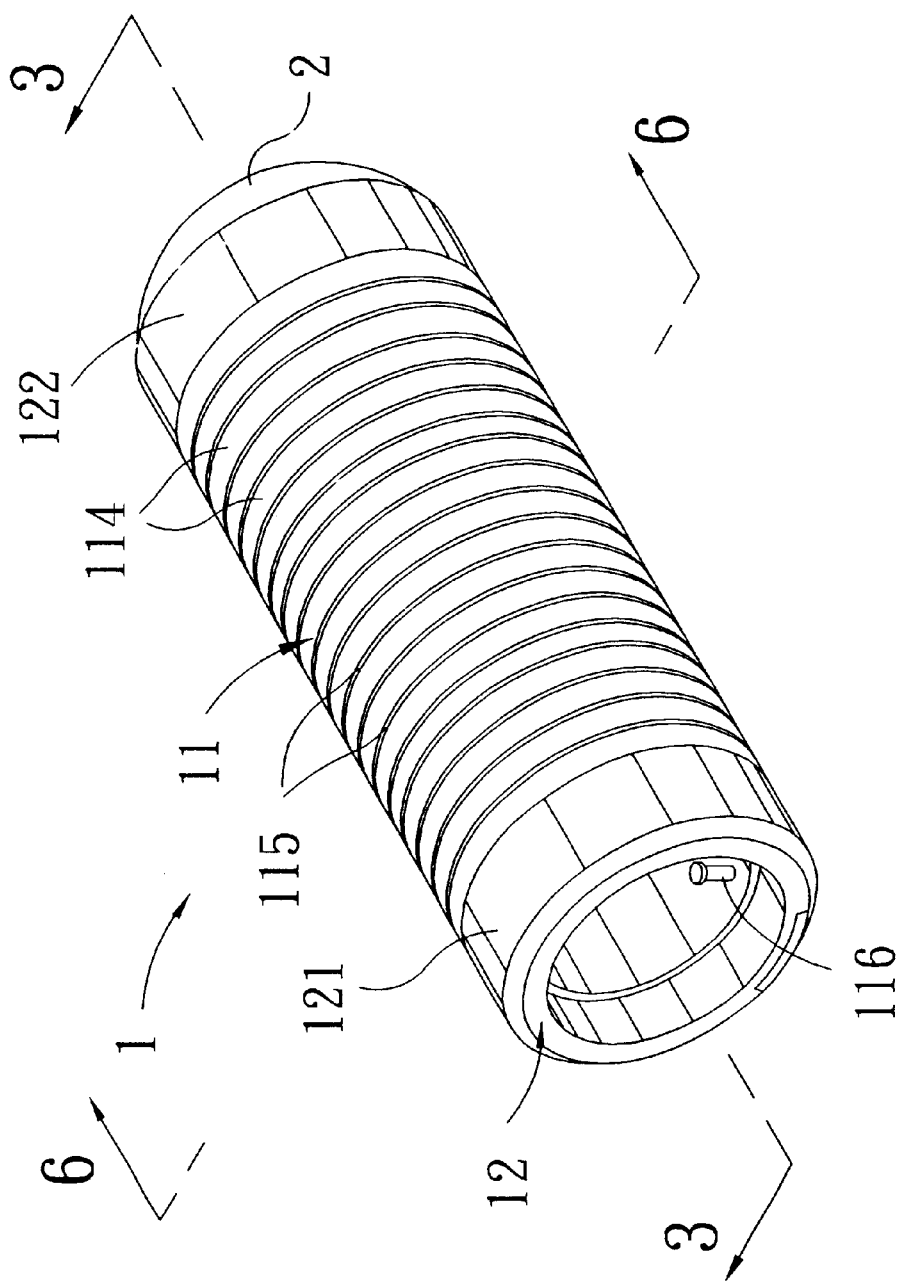
FIG. 2 is a perspective view of the handle sensor of the first embodiment in the present invention.
Figure 3:
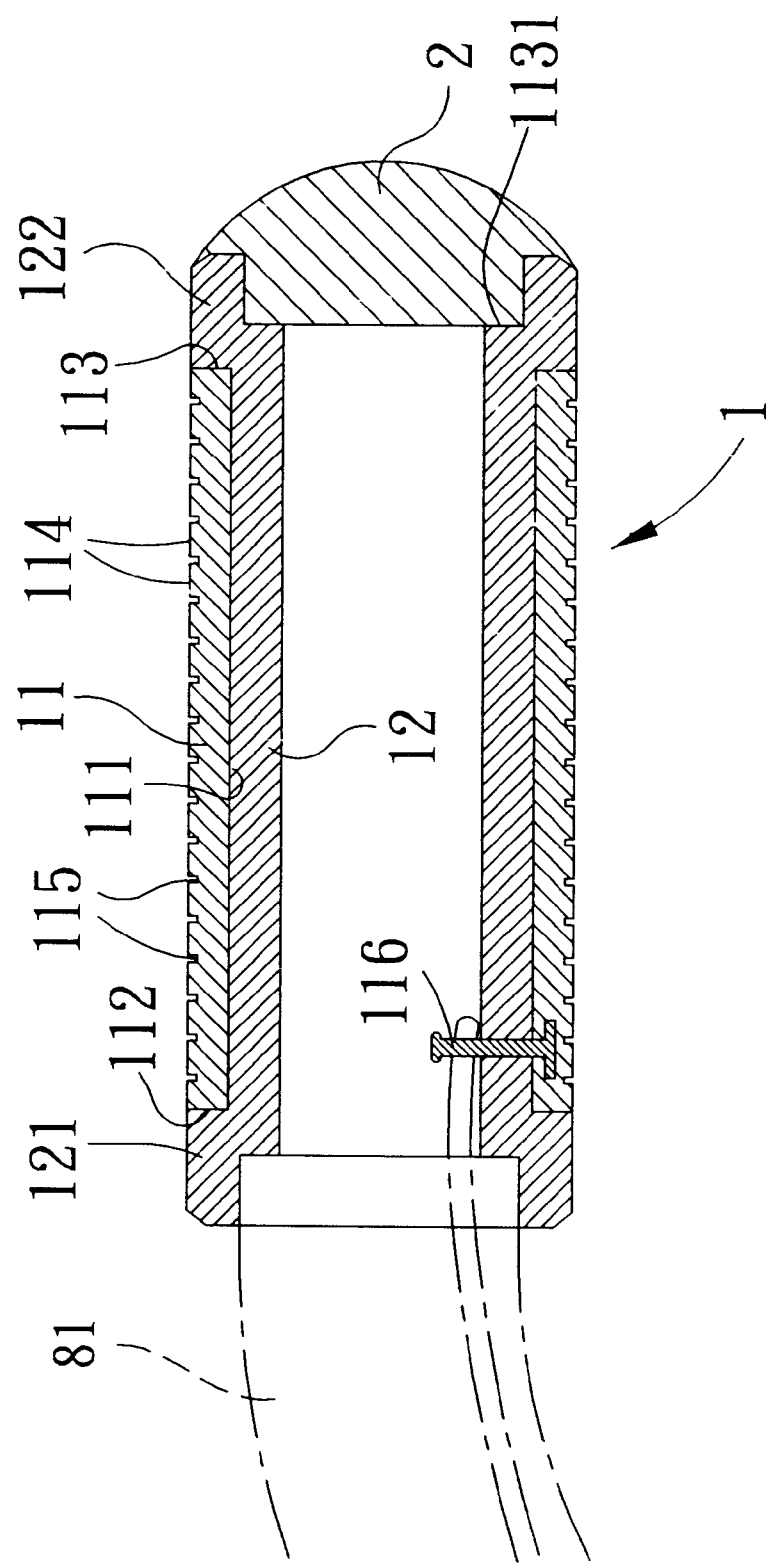
FIG. 3 is a cross-sectional view along the line 3—3 of FIG. 2.
Figure 4:
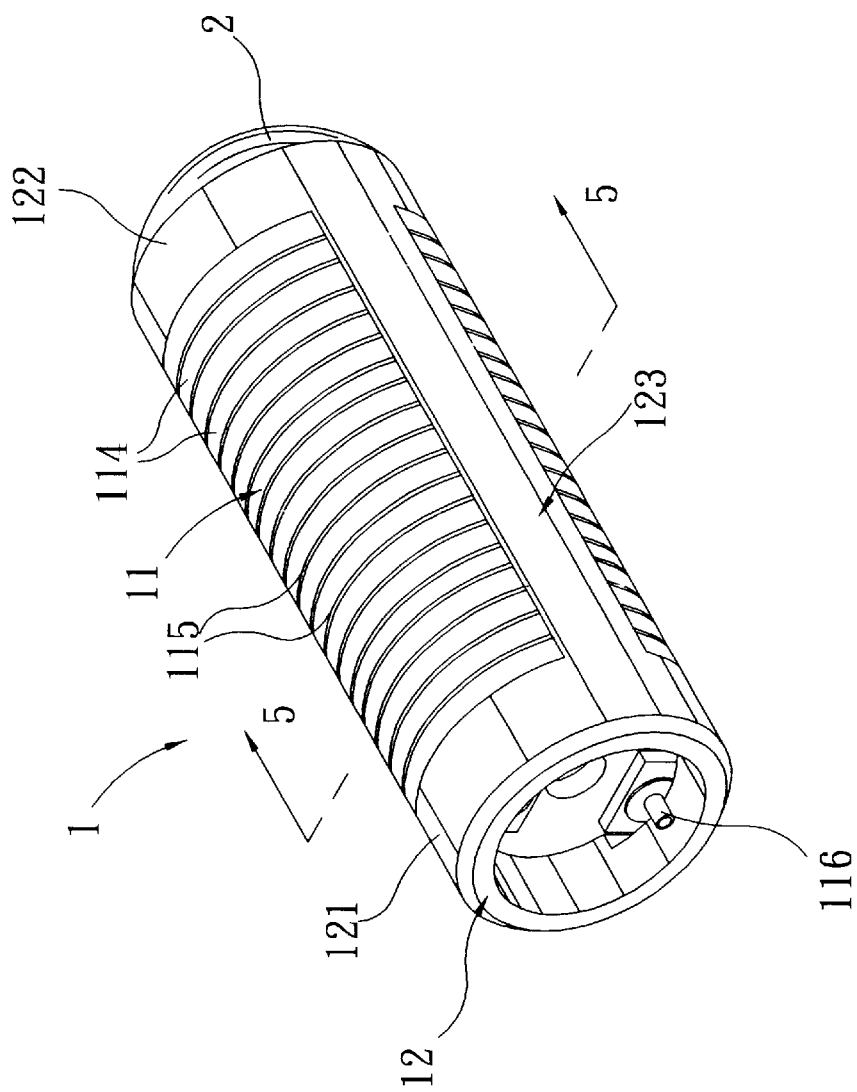
FIG. 4 is a perspective view of the handle sensor of the first embodiment in the present invention similar to that in FIG. 2.

The handle sensor (1) of the present invention is shown in FIG. 1, which is mainly assembled on the tube shape portion of a gymnastic machine, for example on a pair of the handles (81) of a exercising bicycle (8) for being held by an user. Shown in FIGS. 2 and 4 are embodiments of the handle sensor (1). The handle sensor (1) in any embodiment includes a conducting outer layer (11) and an insulating inner layer (12), and both of the two layers are assembled as a tube. Referring to FIG. 3, the bottom (111), left lateral end (112) and right lateral ends (113) of the conducting outer layer (11) are enclosed by the left protecting portion (121) and the right protecting portion (122) of the insulating inner layer (12) so that the conducting outer layer (11) does not at all contact with the exercising bicycle (8), thus the sweat of the user will prevent to flow from the left lateral end (112) or the right lateral end (113) to the metal handle (81) of the exercising bicycle (8). In order to retain the drying of the conducting outer layer (11), a plurality of sweat grooves of the surface (114) of the conducting outer layer (11) for draining sweat.

Figure 7:
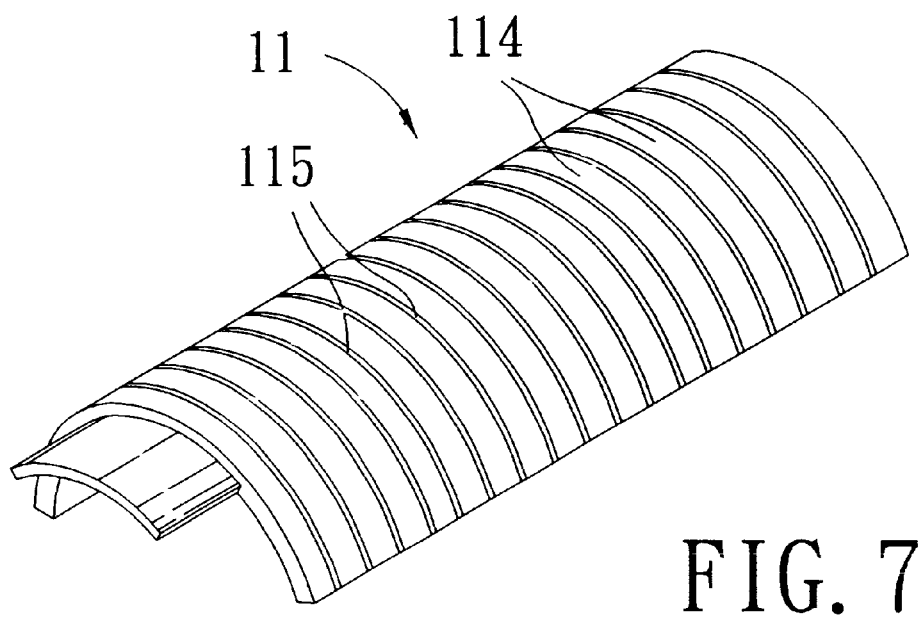
FIGS. 7, 7A, 7B and 7C shows a plurality of depicted examples of half circle for forming the conducting outer layer of FIG. 3.
Figure 7A:
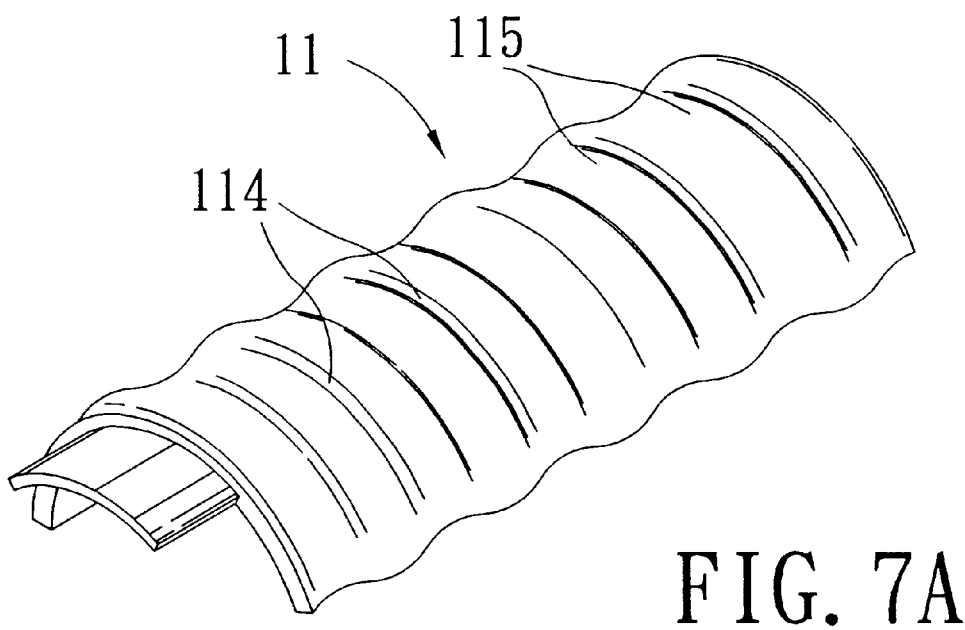
Figure 7B:
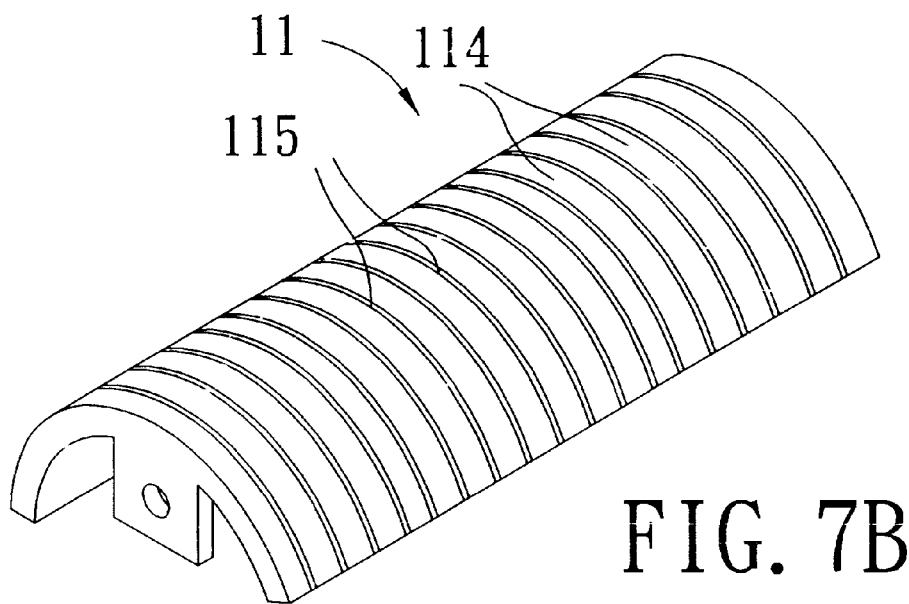
Figure 7C:
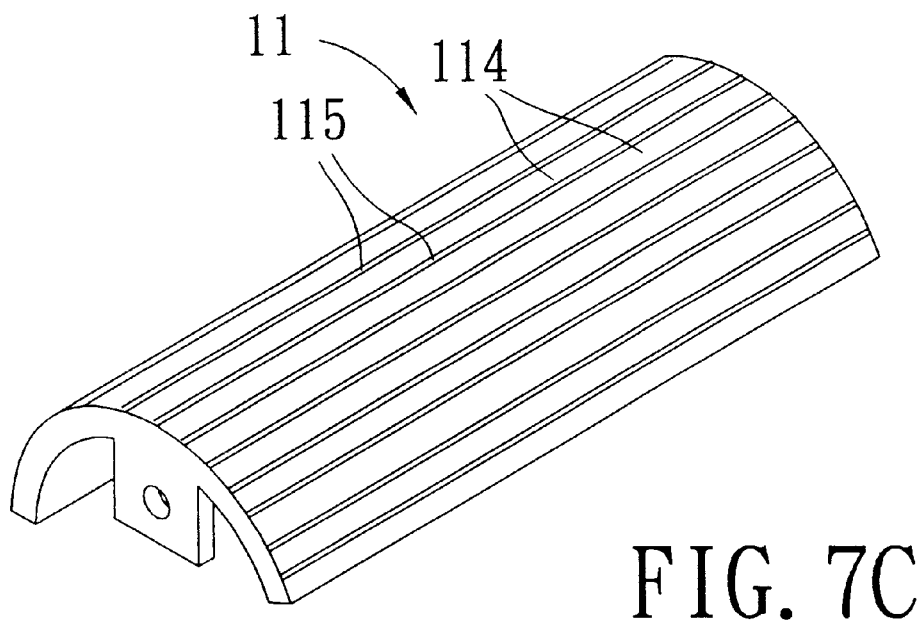

In any embodiment of the handle, a position on the conducting outer layer (11) which will not prevent to assemble with the gymnastic equipment may connect with a conductor (116) for being electrically connected with other components. Since the handle sensor (1) has at least two embodiments as shown in FIGS. 2 and 4. In the handle sensor (1) shown in FIG. 4, the conducting outer layer (11) thereof may be assembled by any two conducting outer layers (11) with half-circles shape shown in FIGS. 7, 7A, 7B and 7C, thus the number of the conductor (116) connected on the handle sensor (1) may be varied according to the forming way of the conducting outer layer (11), for example, the handle sensor (1) shown in the embodiment of FIG. 2 only need one conductor (116), while the handle sensor (1) shown in the embodiment of FIG. 4 at least need to have two conductors (116) for connecting with the two half circle conducting outer layers (11) arranged on the insulating inner layer (12), separately. In order to assist to position the half circle conducting outer layers (11) on the insulating inner layer (12), as shown in FIGS. 7 to 7C, two insulating strips (123) connected, with each others are installed between the left protecting portion (121) and the right protecting portion (122) of the insulating inner layer (12).

Figure 5:
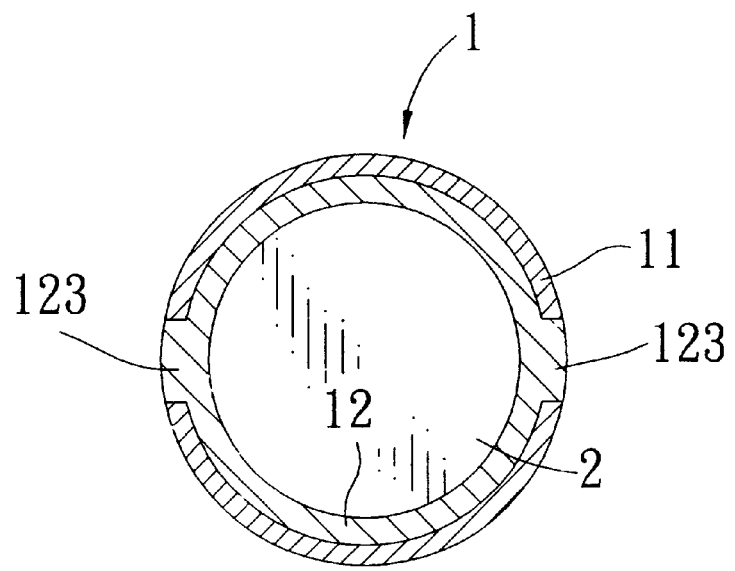
FIG. 5 is a partial cross-sectional view along the line 5—5 of FIG. 4.
Figure 6:
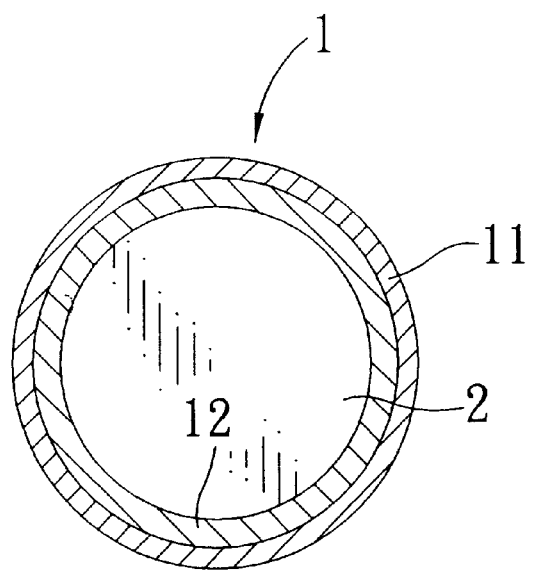
FIG. 6 a cross-sectional view along the line 6—6 of FIG. 2.

The conductor (116) connected on the conducting outer layer (11) of the handle sensor (1) is used in order to be conveniently electrically connected so that the induced potential by the conducting outer layer (11), for example, the pulse of human body of the potential difference of two hands, may be transferred. The embodiment of the conductor (116), for example, is a projecting portion extended integrally from the conducting outer layer (11), or an independent element connected on the conducting outer layer (11). The induction potential signal transferred will be processed by the embodiments shown in FIGS. 8 to 16 as described hereinafter. On the distal opening of the right lateral end (113) of the tube shape handle sensor (1) (i.e. the right protecting portion (122) of the insulating inner layer (12)) shown in the embodiments of FIGS. 2 and 3 is sealed by a detachable insulating plug (2), and the insulating plug (2) is embodied on the embodiment of FIG. 2, wherein the cross-sectional view of FIG. 2 is shown in FIGS. 5 and 6. In another embodiment, the insulating plug (2) is directly extended from the insulating inner layer (12) so to reduce the possibility of the conductor (116) is interfered by vapor or electromagnetic wave, thus the handle signal induced by the handle sensor (1) may be adjusted by the circuit shown in FIGS. 14 and 16 with a minimum lose.

Figure 8:
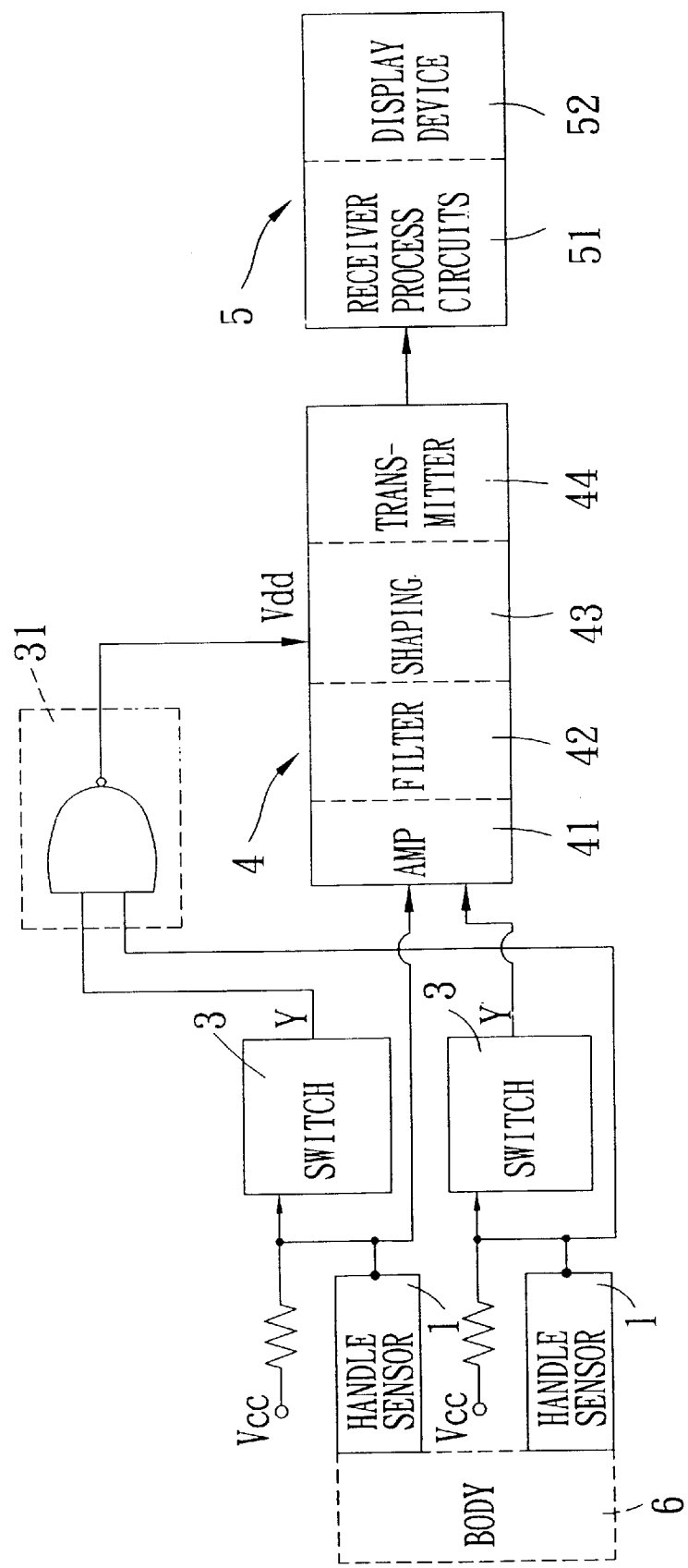
FIG. 8 shows the block diagram of the embodiment of a signal processing circuit the detector of which is handle sensors.

The signal processing circuit device with a detector which is a handle sensor (1) is shown in FIG. 8, wherein the device includes a pair of tube shape handle sensors (1) described in said any embodiment, any of the handle sensors (1) is formed as a current stub of the working switch (3) the power of which is supplied by a rated power source (Vcc), for example, a proper direct current with a voltage of 1.5V or 12V, the power supply from. the rated power source (Vcc) to a pair processing circuit (4) by the working switch (3) is decided according to the holding or releasing of the human body (6) to the handle sensor (1). When the human body (6) holds the handle sensor (1), the processing circuit (4) may derive the working power (Vdd) supplied by the rated power source (Vcc) so to be disabled. The function of the processing circuit (4) is used to accept the reaction signal of the handle sensor (1) and then to amplify, filter, shape and output the reaction signal by the internally sequential connected (0.5 Hz–4 Hz)×60 sec response amplifying circuit (41), filtering circuit (42), rectangular shaping circuit (43) and transmitter (44). The reaction switch outputted by the processing circuit (4) is lastly displayed by a receiving processing display device (5). In generally the receiver process circuit (50) has, for example, a receiver process circuit (51) being a module circuit or an integrated circuit, and a display device (52) controlled by said receiver process circuit (51).

Figure 9:
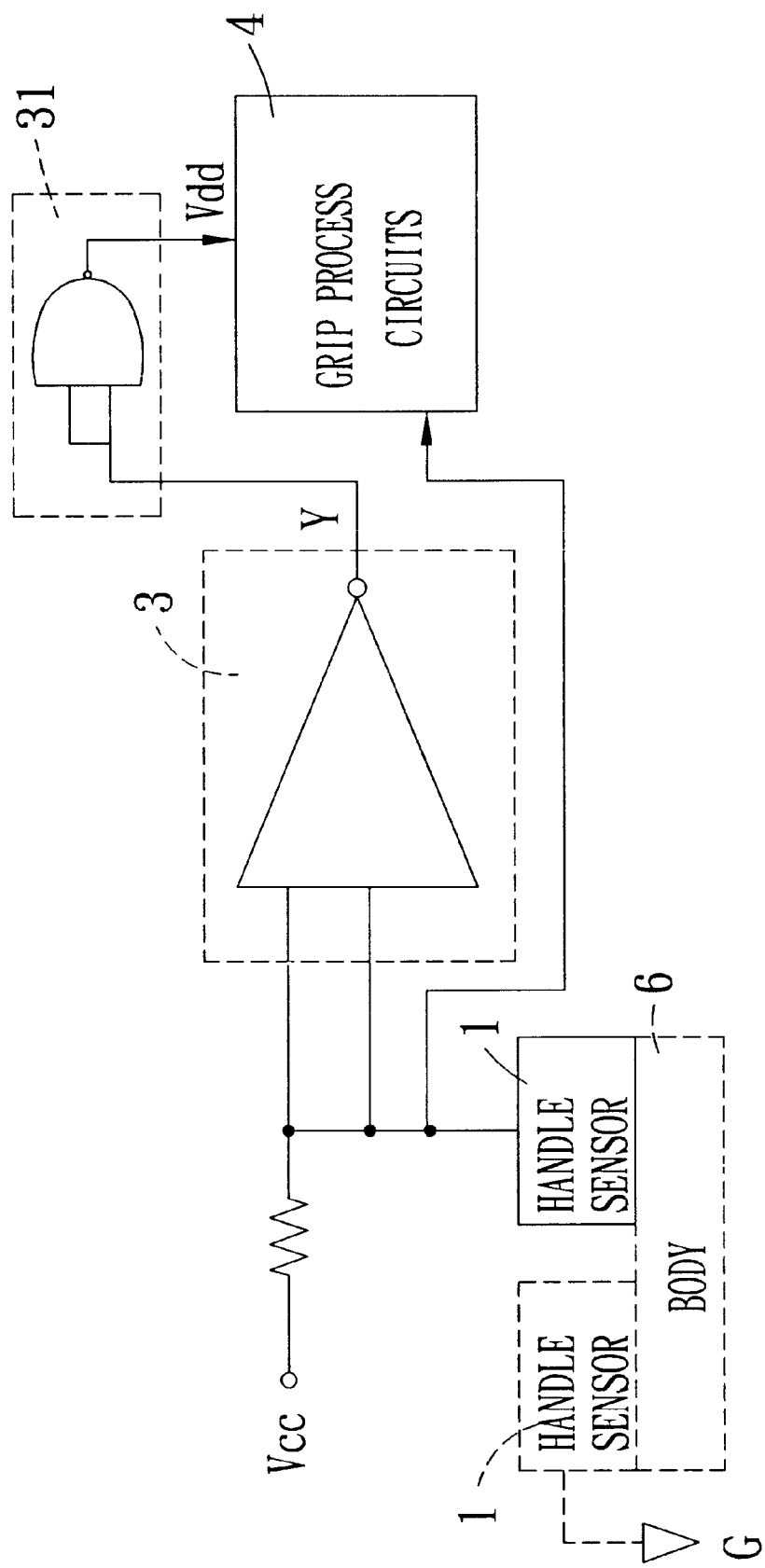
FIG. 9 shows an embodiment of the working switch of FIG. 8.
Figure 10:
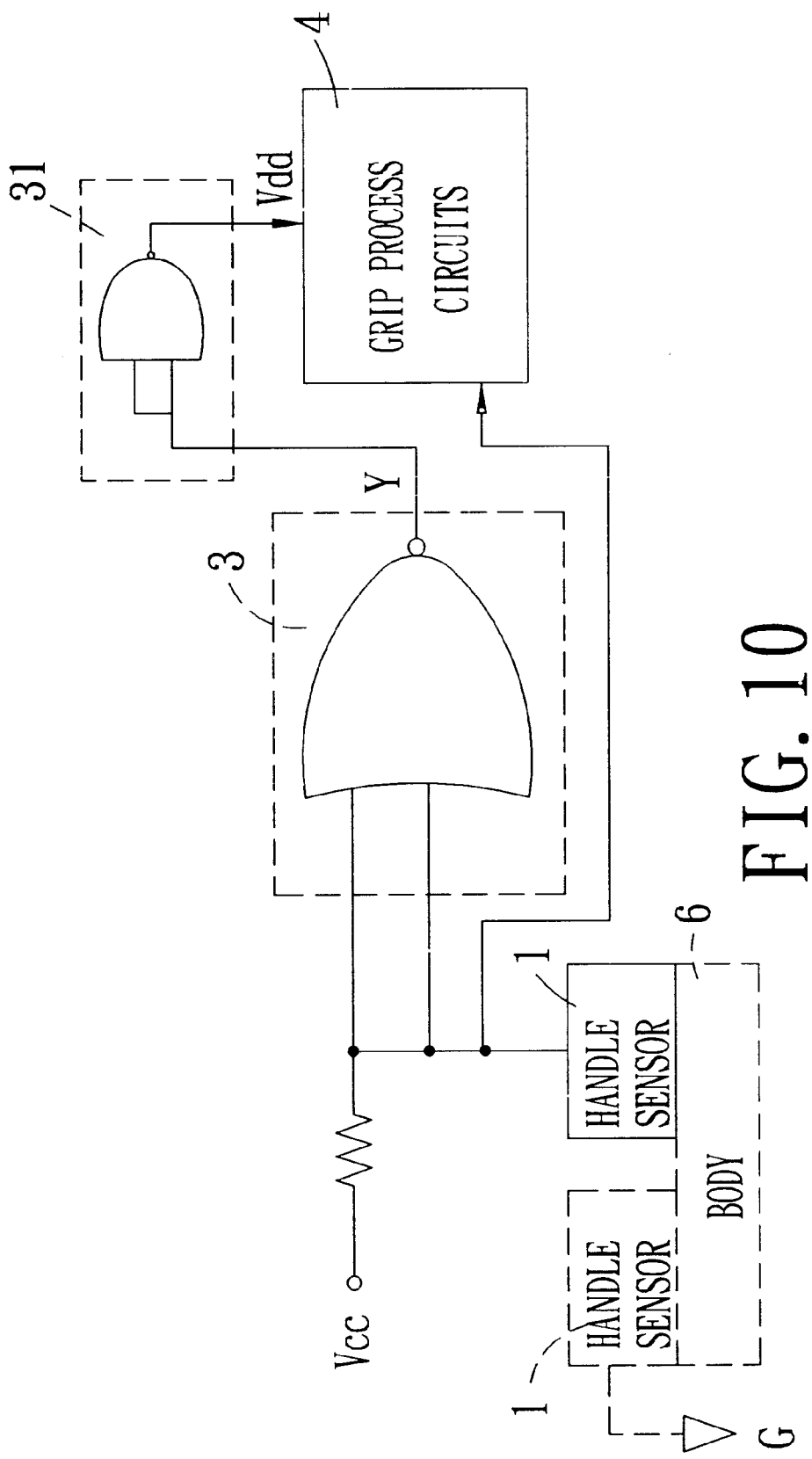
FIG. 10 is another embodiment of the working switch similar to that of FIG. 9.
Figure 11:
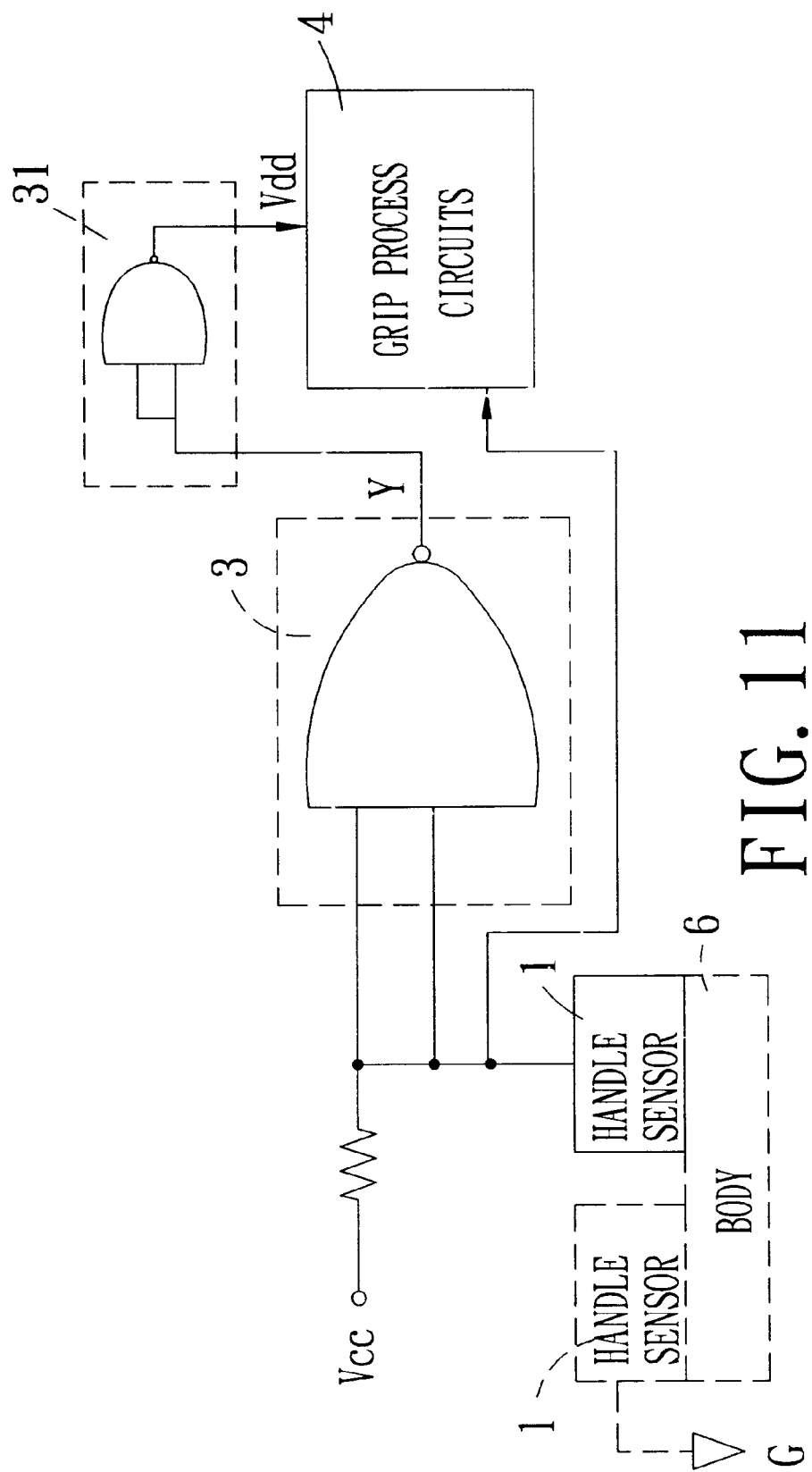
FIG. 11 is a further embodiment of the working switch similar to that of FIG. 9.
Figure 12:
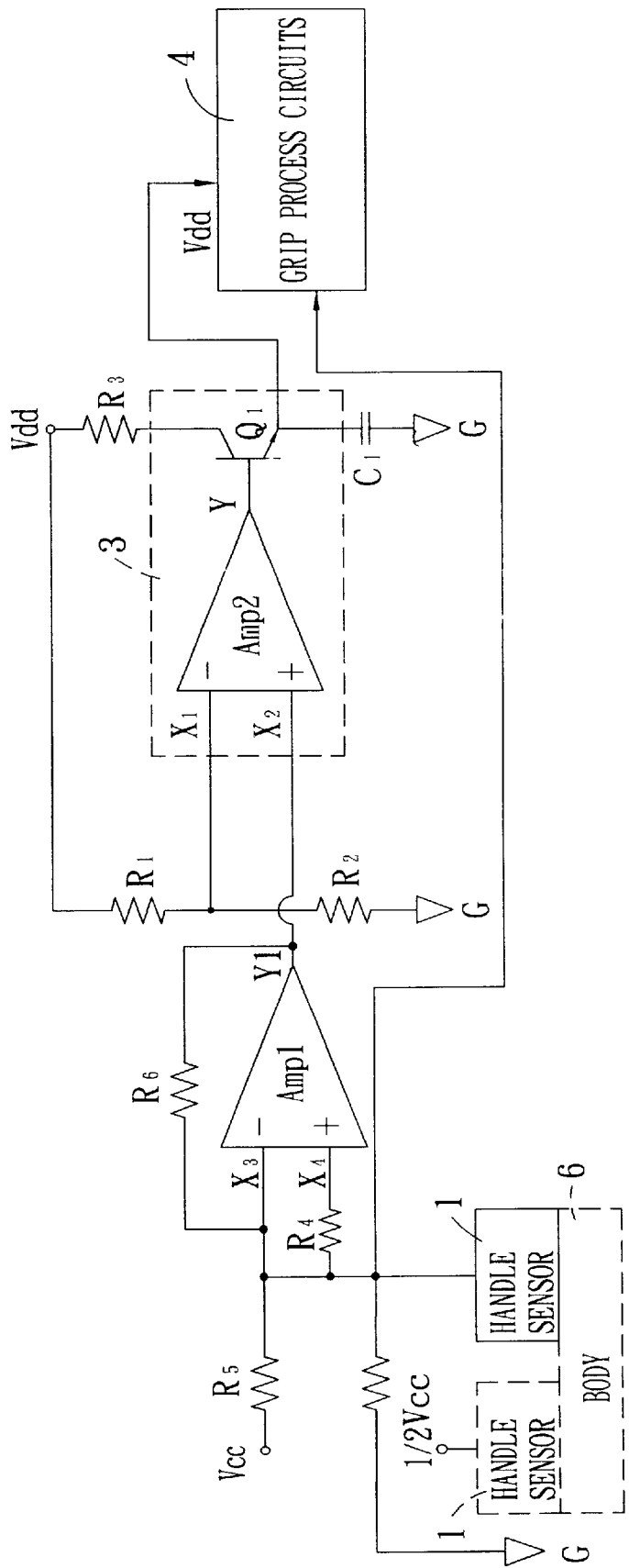
FIG. 12 is a further embodiment of the working switch similar to that of FIG. 9, especially an analog working switch is shown.

In order to prove that the handle sensor (1) is intentionally held by a human body (6), or is an atmosphere impulse inputting to the handle sensor (1) and having a potential near that of a human body, thus the switch on the output terminal (Y) of the working switch (3) may be further adjusted by an adjuster (31) so to prevent a fault signal to enable the processing circuit (4), thus the malfunction of the processing circuit (4) is reduced and the power wasting is prevented. Various embodiments of the working switch (3) of FIG. 8 are, shown in FIGS. 9 to 12, wherein the embodiments of the working switch (3) shown in FIGS. 9 to 11 are logic switch and the embodiment of the working switch (3) shown in FIG. 12 is an analog circuit comparing switch. In FIGS. 9 to 11, a pair of handle sensor (1) uses in common a conducting loop to form a rated power source (Vcc) to supply power to the current stub of the working switch (3), wherein a handle sensor (1) has a conducing loop for transmitting the reaction signal of the handle sensor (1) to the processing circuit (4) so that as the handle sensor (1) is held by a human body (6), the processing circuit (4) not only may derive a working voltage (Vdd), but also amplify, filter, shape and output the reacting signal of the handle sensor (1) using the internal circuits shown in FIG. 8. The primary working theory is that: as the human body (6) holds the handle sensor (1) or the pair of handle sensors (1) by respective one hand or two hands, the current of the rated power source (Vcc) will flow to the ground through the human body (6) or to the human body (6) so that the rated power source (Vcc) present as a low potential on the input direction the working switch (3), such as the NOT gate of FIG. 9, or the NOR gate of the FIG. 10, or the NAND gate of FIG. 11. By the logic characteristic of the working switch (3), a high potential output near the potential of the rated power source (Vcc) is outputted in the direction of the output terminal (Y) of the working switch (3), the high potential output will become the working voltage (Vdd) for pushing the processing circuit (4) so that the processing circuit may process the human body pulse from another conducting loop or the signal of the potential difference of two hands. The potential difference of the two hands only generates as the handle sensors (1) is held by human body (6). While a pair of disconnected handle sensor (1) may be employed to transfer the potential difference signal of the two hands to a processing circuit (4) since the potential of the human body (6) is not equilibrium and the human body (6) is not a well conductor. In the embodiments shown in FIGS. 9 to 11, the working switch (3) of the logic element has at least a working switch (3) and the signal of the output terminal (Y) of the working switch (3) may output voltage to a processing circuit (4) after being adjusted by an adjuster such as an AND gate.

As shown in FIG. 12. the comparing amplifier (AMP2) of the working switch of the analog circuit has two input terminals, for example a first input terminal (X2) and a second input terminal (X2), wherein an input terminal, for example the second input terminal (X2), may be used to extract the voltage of the output terminal (Y1) of the preamplifier (AMP1) as the comparing input voltage of the comparing amplifier (AMP2), the other end of the comparing amplifier (AMP2), for example, the first input terminal (X1), is connected with a voltage dividing circuit formed by a resistor (R1) and a resistor (R2), wherein the resistor, for example resistor (R1) is also connected with a rated power source (Vcc) so that the first input terminal (X1) may provide a reference potential through the ratio of the resistors (R1) and (R2) to a comparing amplifier (AMP2). Another, the rated power source (Vcc) is connected to a switch (Q1) through a resistor (R3) so that the switch (Q1) has a potential difference between the two input terminals (X1) and (X2) of the comparing amplifier (AMP2), thus it is turned on. In order to provide a steady working voltage (Vdd) to the processing circuit (4), a charger, for example a capacitor (C1), is connected with the output terminal of the working voltage (Vdd) of the switch (Q1) in series and by the charging of the capacitor (C1) the working voltage (Vdd) may often in a saturation condition.

As for a preamplifier (AMP1) for providing a comparing voltage to a second input terminal (X2) of the comparing amplifier (AMP2) shown in FIG. 12 it has at least two input terminals, for example a third input terminal (X3) and a fourth input terminal (X4), wherein the input terminal, for example the third input terminal (X3), is connected with a pair of handle sensor (1) for being held by human body (6), and is connected with a power source (½ Vcc) approximately equal to one half of the rated power source (Vcc) supplied to the comparing amplifier (AMP2). A resistor (R4) having a small resistance (r4) is connected between the fourth input terminal (X4) and the handle (1). Further the voltage difference on the resistor (R4) is used as a parameter for calculating the voltage of the output terminal (Y1) of the preamplifier (AMP1), the decision of the parameter is also matched with a resistor (R5) connected the third input terminal (X3) and a feedback resistor (R6) connected between the output terminal (Y1) of the comparing amplifier (AMP2) and the third input terminal (X3). Assuming the resistance (r5) of the resistor (R5) is not equal that the resistance (r6) of the resistor (R6), then the voltage (V1) of the output terminal (Y1) of the preamplifier (AMP1) is listed in the following:

$$V1=(r5+r6)\times \tfrac{1}{2}Vcc\times r4\div r5$$

As a pair of handle sensors (1) located on the tube portion of the gymnastic machine have not been held, then the output terminal (Y1) of the preamplifier (AMP1) will not output any voltage. Therefore, the second input terminal (X2) of the comparing amplifier (AMP2) has no any input voltage, thus the differential voltage will not been outputted for pushing the switch (Q1). Inversely, As one of the pair of handle sensors (1) located on the tube portion of the gymnastic machine has held by human body (6), a voltage about ½ Vcc will be generated on the output terminal (Y1) of the preamplifier (AMP1) (assume the resistor (R5) is equal to resistor (R6)), wherein the ½ Vcc voltage is a comparing output voltage of the second input terminal (X2) of the comparing amplifier (AMP2) and is comparing with the reference voltage of the first input terminal (X1) so that a differential voltage is generated on the output terminal (Y) of the comparing amplifier (AMP2) and is electrically conducted with said pushing switch (Q1), thus the current of rated power source (Vcc) may flow to the processing circuit (4) through the switch (Q1) as a power source for enable the processing circuit (4). While the pulse from the human body holding the handle sensor (1) or the differential potential of two hands may be amplified, filtered, shaping and output on the processing circuit (4) through the conducting loop between the handle (1) and the processing circuit (4).

Figure 13:
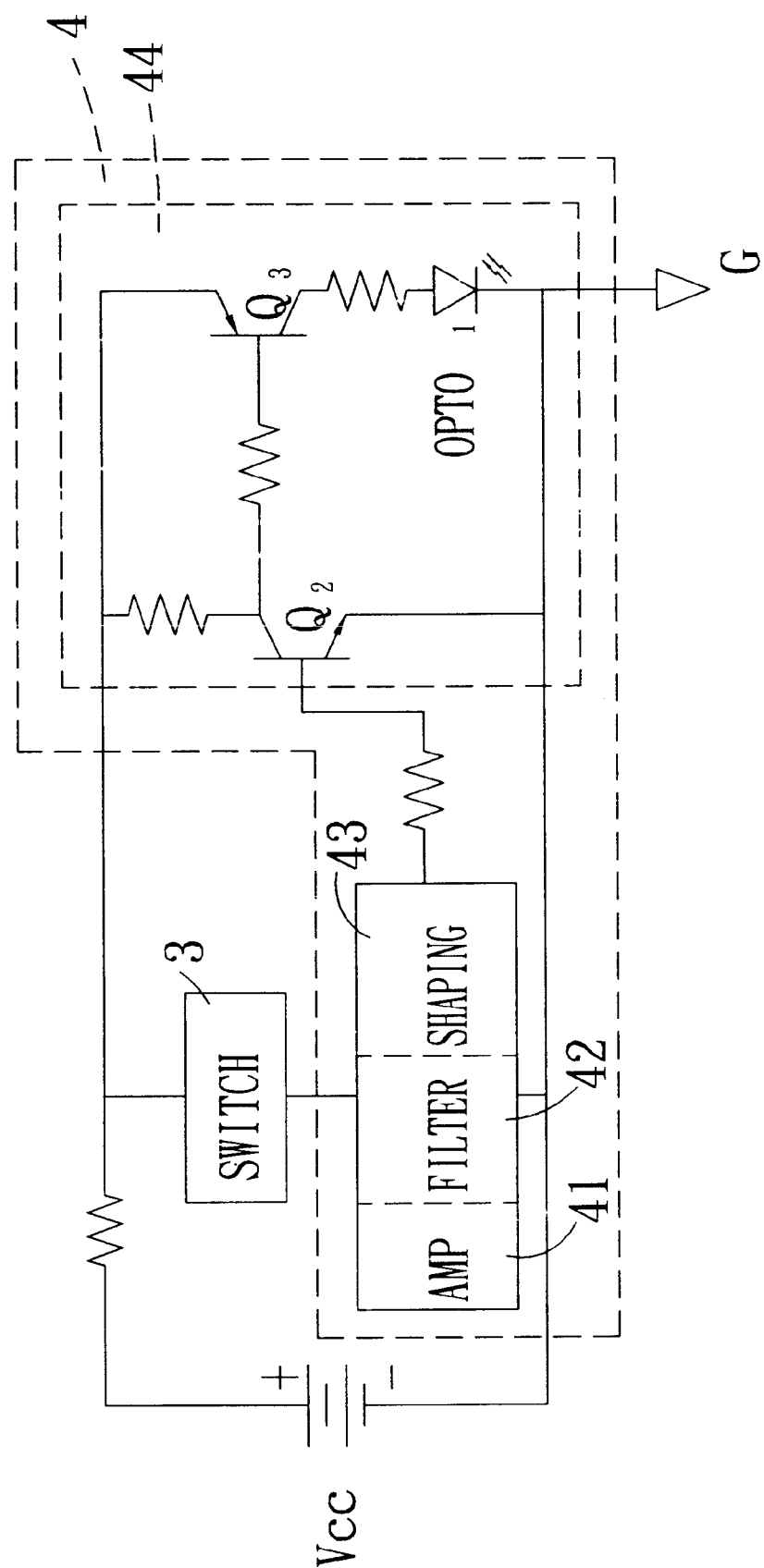
FIG. 13 shows an optic coupling transmitter which may be connected with any of the working switches and processing circuits in the embodiments shown in FIGS. 9 to 12.
Figure 14:
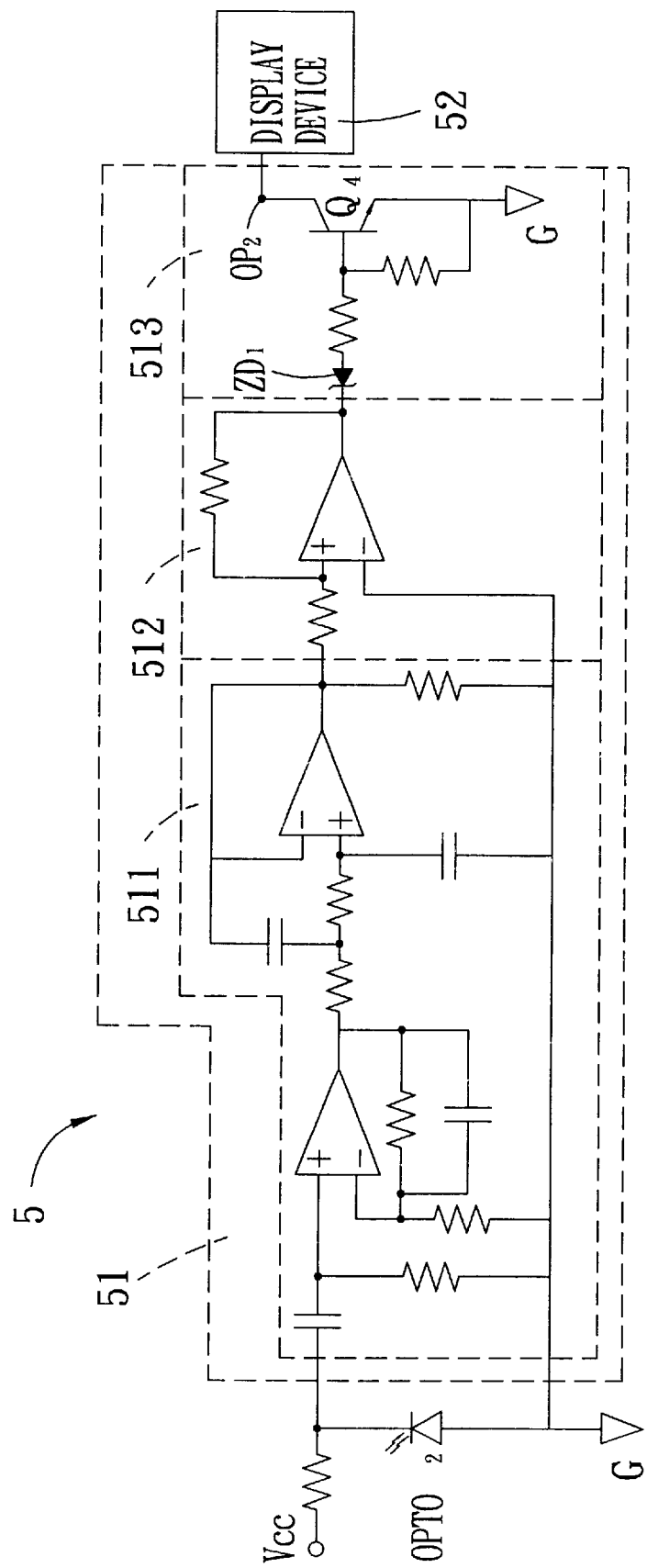
FIG. 14 shows the display processing circuit of FIG. 13.
Figure 15:
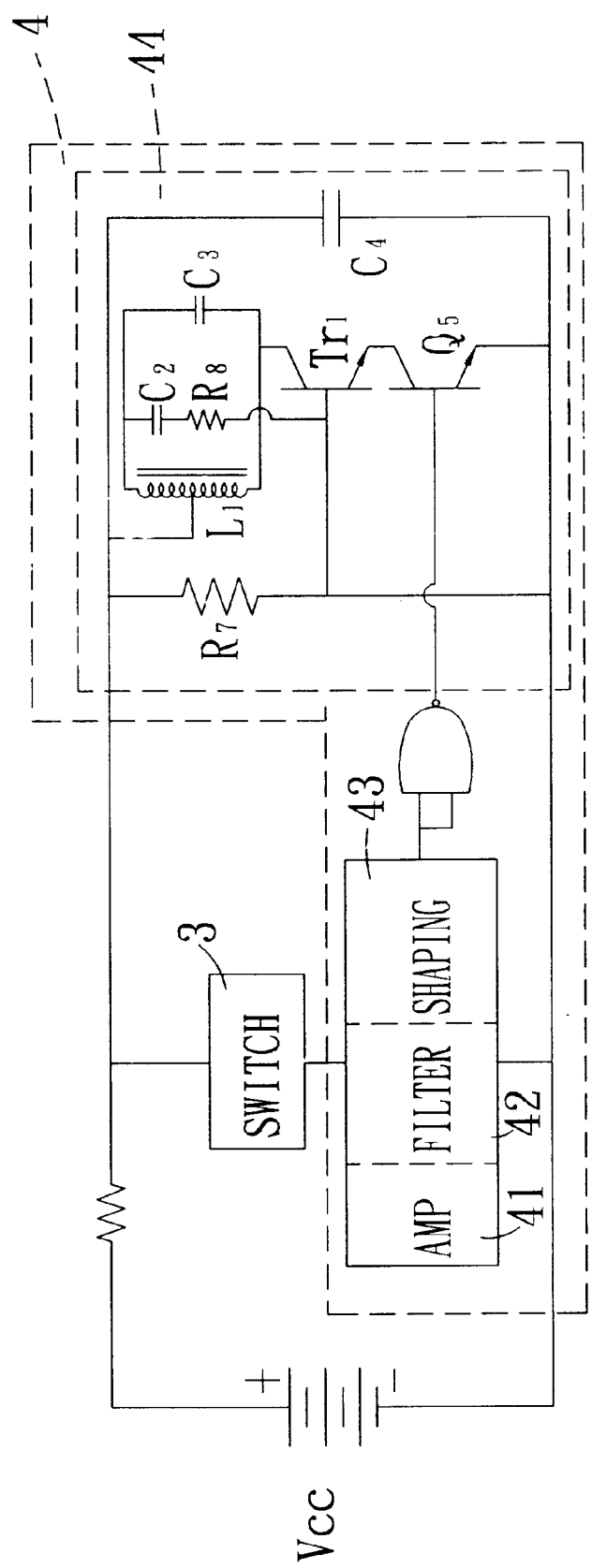
FIG. 15 shows a radio frequency transmitting circuit which may be connected with any of the working switches and processing circuits in the embodiments shown in FIGS. 9 to 12.
Figure 16:
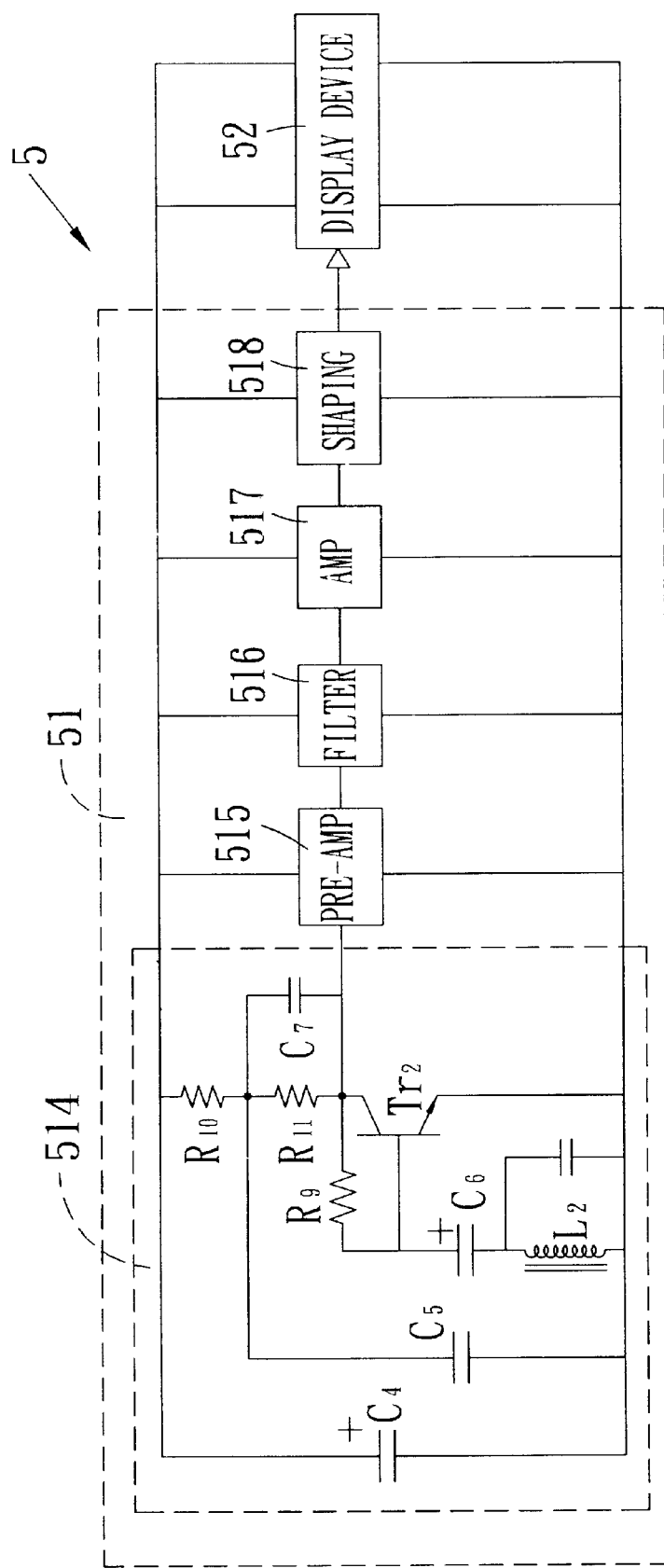
FIG. 16 shows the display circuit of FIG. 15.

FIGS. 13 and 15 shows the embodiment of the transmitter (44) of the processing circuit (4), wherein FIG. 13 has a type of optic coupling transmitter, while FIG. 15 has a type of radio frequency transmitting circuit. The optic coupling transmitter in FIG. 13 includes a current amplifying circuit formed by a set of transistor (Q2) and (Q3), and an optic coupling element (OPTO1) emitted by said current amplifying circuit so that the pulse from the human body (6) holding the handle, sensor (1) or the differential potential of two hands may be transferred through the processing of the response amplifying circuit (41), the filtering circuit (42), and the rectangular shaping circuit (43) of the processing circuit (4) for being receiving, restoring and displaying by an optic frequency processing and displaying device (5) shown in FIG. 14, the optic frequency processing and displaying device (5) includes a receiver process circuit (51) and a display device (52). The receiver process circuit (51) use an optic coupling element (OPTO2) to generate an optic frequency coupling signal of the. optic coupling element (OPTO1) and use a filtering amplifier (511) interconnected on the second stage of the optic coupling element (OPTO1) to filter and properly amplify the noises of the pulse from the human body (6) holding the handle sensor (1) or the differential potential of two hands generate during optic coupling. In order to avoid the interference from higher order harmonic, the filtering amplifier is preferred at least two stages for compensating the transmission loss during receiving and transmitting. The filtered and amplified pulse from the human body (6) holding the handle sensor (1) or differential potential of two hands are further interconnected with an amplifier on the second stage for further being amplifying so that a voltage shaping element, for example, a shaping circuit (513) mainly formed by a Zener diode (ZD1) and switch (Q4) may extract a amplifying signal outputted by an amplifier circuit (512) and confine the shape of the signal lastly a display device, for example a computer terminal, a scope, a plotter, a printer or a number display may extract the shaped signal from the output terminal (OP2) of the switch (Q4) and then output the signal.

Another transmitter is the radio frequency emitting circuit shown in FIG. 15, the signal emitted by said radio frequency emitting circuit is the pulse from the human body (6) holding the handle sensor (1) or the differential potential of two hands through the processing of the response amplifying circuit (41), the filtering circuit (42), and the rectangular shaping circuit (43) of the processing circuit (4). The output rectangular wave outputted by the rectangular shaping circuit (43) is used to trigger the switch (Q5) on the radio frequency emitting circuit and caused that an oscillating circuit formed mainly by an oscillating crystal (Tr1) and auxiliary by resonance components, for example resistors (R7 and R8), capacitors (C2, C3 and C4) and inductor (L1) to generate a modulate frequency for example 5 KHz to transmit the pulse of the human body (1) or the static differential potential of two hands. The receiver process circuit (51) of the processing display device (5) has a resonance receiving circuit formed mainly by an oscillating crystal (Tr2) and auxiliarily by resonance components, for example resistors (R9, R10, and R11), capacitors (C4, C5, C6 and C7) and inductor (L1) for taking up the pulse of the human body (1) or the static differential potential of two hands loading from the modulating frequency of 5 KHz and transmits a preamplifier for further amplifying. This signal may be successfully transmitted to a second stage filter (516) for filtering noises, wherein in order to compensating the decaying during the filter (516) so the signal is further inputted toga first stage amplifier (517) to enhance the signal and further by a second integrate shaping circuit (517) to adjust the sinusoidal gaining signal to a continuous rectangular wave with a uniform signal strength, thus it may be displayed by a display (52) controlled by a microprocessor, for example, a computer terminal, a scope, a plotter, a printer or a number display.

Although certain preferred embodiment of the present invention has been shown and described in detail, it should be understood that various changes and modification may be made therein without departing from the scope of the appended claims.

What is claimed is:

1. A pair of tubular handle sensors adapted to be used on handles of an exercising device, each said handle sensor comprising:
    a tubular insulating layer installed on the handle of the exercising device; and
    a conducting layer having at least an upper surface exposed so as to serve as an electrical contact element, said conducting layer being enclosed by said insulating layer except for said upper surface, with a plurality of grooves being installed on said upper surface of said conducting layer.

2. The handle sensor according to claim 1 wherein said handle sensor has an end opening which receives a detachable insulated plug.

3. A signal processing circuit comprising:
    a rated power source for providing a direct current high voltage;
    a pair of tubular handle sensors each of which includes an insulating layer and an exposed conducting layer, at least one of said conducting layers is connected to said rated power source;
    a plurality of working switches, each said working switch has at least a first input terminal and an output terminal, said first input terminal receives a high voltage input from said rated power source, at least one of said first input terminals is connected to said conducting layer of said handle sensor;
    a processing circuit for extracting a reaction signal of said handle sensors, said processing circuit is controlled by said working switches to take a working voltage from said rated power source, said processing circuit having-sequentially at least a responded amplified circuit, a filtering circuit for filtering an amplified signal, a rectangular shaping circuit for extracting and shaping a filtered signal, and a transmitter to output a shaped signal;
    wherein at least one of said working switches is a logic element that provides a reversing potential level.

4. A signal processing circuit comprising:
    a rated power source for providing a direct current high voltage;
    a pair of tubular handle sensors each of which includes an insulating layer and an exposed conducting layer, at least one of said conducting layers is connected to said rated power source;
    a plurality of working switches, each said working switch has at least a first input terminal and an output terminal, said first input terminal receives a high voltage input from said rated power source, at least one of said first input terminals is connected to said conducting layer of said handle sensor;
    a processing circuit for extracting a reaction signal of said handle sensors, said processing circuit is controlled by said working switches to take a working voltage from said rated power source, said processing circuit having sequentially at least a responded amplified circuit, a filtering circuit for filtering an amplified signal, a rectangular shaping circuit for extracting and shaping a filtered signal, and a transmitter to output a shaped signal;
    wherein at least on of said working switches is an analog amplifying comparing circuit including a preamplifier having at least two input terminals and one output terminal, and a comparing amplifier having at least two input terminals and one output terminal; said preamplifier is connected to said handle sensors and an output terminal thereof is connected to one input terminal of said comparing amplifier so as to compare with a reference voltage on another input terminal of said comparing amplifier, thus when said handle sensors are held, a differential voltage is generated for pushing a switch.

5. A signal processing circuit comprising:
    a rated power source for providing a direct current high voltage;
    a pair of tubular handle sensors each of which includes an insulating layer and an exposed conducting layer, at least one of said conducting layers is connected to said rated Dower source;
    a plurality of working switches, each said working switch has at least a first input terminal and an output terminal, said first input terminal receives a high voltage input from said rated power source, at least one of said first input terminals is connected to said conducting layer of said handle sensor;

a processing circuit for extracting a reaction signal of said handle sensors, said processing circuit is controlled by said working switches to take a working voltage from said rated power source said processing circuit having sequentially at least a responded amplified circuit, a filtering circuit for filtering an amplified signal, a rectangular shaping circuit for extracting and shaping a filtered signal, and a transmitter to output a shaped signal;

wherein at least one of said working switches has at least one input terminal which is connected in parallel with said first input terminal and any input terminals may be used to form a connection with said conducting layer of said handle sensors.

* * * * *